(12) United States Patent
Minogue

(10) Patent No.: US 12,007,346 B2
(45) Date of Patent: Jun. 11, 2024

(54) ELECTRICAL INSULATION IN GARMENTS

(71) Applicant: BIO-MEDICAL RESEARCH LTD, Galway (IE)

(72) Inventor: Conor Minogue, Galway (IE)

(73) Assignee: BIO-MEDICAL RESEARCH LTD, Galway (IE)

( * ) Notice: Subject to any disclaimer, the term of this patent is extended or adjusted under 35 U.S.C. 154(b) by 238 days.

(21) Appl. No.: 17/601,253

(22) PCT Filed: Apr. 3, 2020

(86) PCT No.: PCT/EP2020/059608
§ 371 (c)(1),
(2) Date: Oct. 4, 2021

(87) PCT Pub. No.: WO2020/201528
PCT Pub. Date: Oct. 8, 2020

(65) Prior Publication Data
US 2022/0178858 A1      Jun. 9, 2022

(30) Foreign Application Priority Data

Apr. 5, 2019   (GB) ..................... 1904831

(51) Int. Cl.
*G01N 27/04*      (2006.01)
*A41D 1/00*       (2018.01)
(Continued)

(52) U.S. Cl.
CPC ............ *G01N 27/04* (2013.01); *A41D 1/002* (2013.01); *A41D 31/265* (2019.02); *H01B 5/14* (2013.01)

(58) Field of Classification Search
CPC ........ A41D 1/002; A41D 31/265; A61B 5/25; A61B 5/6805; A61N 1/0484; G01N 27/04;
(Continued)

(56) References Cited

U.S. PATENT DOCUMENTS 5,157,379 A * 10/1992 Dennison ............... A61B 42/30
                                                    128/897
7,810,172 B2 * 10/2010 Williams ........... A41D 13/1236
                                                    2/114

(Continued)

FOREIGN PATENT DOCUMENTS

| CN | 108601409 | 9/2018 |
| JP | 2018-087398 A | 6/2018 |
| JP | 2018-104869 A | 7/2018 |

OTHER PUBLICATIONS

International Preliminary Report on Patentability on PCT Appln. PCT/EP2020/059608 dated Oct. 14, 2021.

(Continued)

*Primary Examiner* — Vinh P Nguyen
(74) *Attorney, Agent, or Firm* — Foley & Lardner LLP

(57) ABSTRACT

An electrical system with conductive and insulating layers for application to a surface of a garment is disclosed. The electrical system includes a first insulating layer for attaching to a garment, a second insulating layer, and an electrically conductive layer encapsulated between the first insulating layer and the second insulating layer. The first and second insulating layers have a predetermined minimum voltage withstand and a predetermined minimum resistance.

24 Claims, 3 Drawing Sheets

(51) Int. Cl.
*A41D 31/26* (2019.01)
*H01B 5/14* (2006.01)

(58) Field of Classification Search
CPC ...... H01B 5/14; H05K 1/0256; H05K 1/0283; H05K 2201/09472; H05K 3/0058
See application file for complete search history.

(56) References Cited

U.S. PATENT DOCUMENTS

| | | | |
|---|---|---|---|
| 8,948,839 B1* | 2/2015 | Longinotti-Buitoni | ..................... A61B 5/6806 600/382 |
| 10,973,413 B2* | 4/2021 | Rapp | ......................... A61F 5/00 |
| 11,246,213 B2* | 2/2022 | Longinotti-Buitoni | ..................... D06P 1/5285 |
| 2010/0234715 A1* | 9/2010 | Shin | ....................... A61B 5/282 66/171 |
| 2015/0004282 A1 | 1/2015 | Mills | |
| 2016/0007475 A1 | 1/2016 | Zanesi | |
| 2017/0340226 A1 | 11/2017 | Takagahara et al. | |

OTHER PUBLICATIONS

International Search Report and Written Opinion on PCT/EP2020/059608 dated Jun. 10, 2020.
Japanese Office Action on JP Appln No. 2021-559307, dated Nov. 28, 2023 (8 pages, including English translation).

\* cited by examiner

ELECTRICAL INSULATION IN GARMENTS

CROSS-REFERENCE TO RELATED APPLICATIONS

This application is a U.S. National Stage Application under 35 U.S.C. § 371 of International Patent Application No. PCT/EP2020/059608, filed on Apr. 3, 2020, which claims priority to Great Britain Patent Application No. 1904831.3, filed on Apr. 5, 2019, the content of each of which is incorporated herein by reference in their entireties

FIELD OF THE INVENTION

The present invention relates to insulation that is provided in garments that incorporate electrical elements.

BACKGROUND TO THE INVENTION

Garments that incorporate electrical wiring are becoming common with many applications emerging such as physiological and biomechanical sensing, heating, electrical stimulation, lighting for visibility, user interfacing etc. The fundamental purpose of such wiring is to convey electrical signals or currents from one part of the garment to another, for example from a set of skin-contacting electrodes located at the chest to an electronic module located elsewhere in the garment. Clearly such wiring, and any insulation provided with it, needs to be flexible and capable of withstanding the range of forces that arise in putting on and taking off the garment, as well as wearing, washing drying and storing it. The garment will generally have to operate across a range of temperature and humidity, as well as other environmental conditions such as fluid and dust exposure. If it has to be washed, then the wiring needs to withstand the chemical and mechanical conditions involved.

There are now many different options for creating such wiring including copper wire between fabric layers or within seams, printed circuits using screen printed conductive inks, 3D printing, conductive thread in the form of yarn or textiles, thin sheets or strips of conductive polymers or elastomers. The electrical resistance of such conductors is often an important factor, in particular, the stability of the resistance in response to stretching, bending, washing etc.

In most cases there is a requirement for insulation between conductors to ensure correct functioning of the device. There are many options for providing insulation such as printed dielectric inks or encapsulants, extruded sheets of insulating material that are cut to the required shape, injection moulded plastics, 3D printed material. Conductive threads can be coated with an insulating film.

Of particular interest is where the electrical system in a garment is made up of several layers that are applied to the textile or fabric surface 1, for example (see FIG. 1):

An adhesive layer 3 attaching the structure to the fabric of the garment
An insulating layer 5
A conductive layer 7
An insulating layer 9

This structure can be applied to the skin facing surface of the garment, the outer surface, or indeed between textile layers of the garment. One or both insulating layers 5, 9 may have apertures 11 (see FIG. 2) to allow electrical connection to the underlying conductive layers 7. The textile also may have an aperture 15 to allow access to the exposed conductor.

In order to achieve a flexible and lightweight finished garment it is desirable that these layers are as thin and as flexible as possible. It is also necessary that the conductive layer 7 retains a minimum conductivity during stretch and bending and that the insulating layers 5, 9 have sufficient resistance and dielectric strength.

Conductive inks are now emerging with good stretch properties that can be printed directly onto stretch fabrics. In addition to wiring there is often a need to make an electrical contact with the skin using one or more electrodes. For example, in electrical stimulation it is desirable to have a defined area of skin contact to ensure that the stimulation current is dispersed at the skin such that high current density is avoided. Electrodes can be made from thin sheets of conductive elastomers, conductive inks, conductive textiles and the like. An electrode can be formed by simply having a window in the overlying insulation layer that exposes the conductive layer. An additional layer can be applied to the electrode area to modify its conductivity, for example, to match its conductivity to that of the skin.

Insulation is necessary to constrain current flow to the desired points in the system. Insulation that is provided to ensure correct functioning of the device by isolating conductors from each other can be described as functional insulation. Insulation may also be necessary to isolate the conductors from their surroundings to ensure safety. The prior art, however, has not addressed the performance requirement for such insulation, let alone its design. This is particularly important when the conductors concerned are patient connections and there is a need to isolate them from ground or to isolate them from contact with parts of the body to which they are not intended to make contact. Such insulation can be referred to as protective insulation. Insulation may of course have both functional and protective purposes.

For example, a conductive track may be printed on the skin facing side of a garment from which leakage of current into the skin is to be avoided. An insulating layer can be applied over the conductive layer which electrically separates it from the skin. Adding an insulating layer overlying the printed conductive track reduces the flexibility of the system and so it is desirable to make it has thin and flexible as possible. On the other hand, it needs to be durable and survive normal wear and tear including washing. The breakdown voltage of a given insulating material depends on its thickness and dielectric strength and so it is necessary to select a thickness which achieves an appropriate balance between flexibility, weight and insulation performance. Insulation at the back of electrodes is also important. Consider a skin-contact electrode located on the skin facing surface of a garment. It is necessary to insulate the opposite face of this electrode such that no current flows through the garment to the outer surface. This is to prevent leakage current to the user who can very likely make finger or hand contact with the exterior surface of the garment. It is not immediately apparent for a given application what the dielectric strength and insulation resistance requirements are for each hazard scenario. For example, if the insulation in a body worn battery operated heater circuit breaks down in one place there is no hazard since there would be no return path for any leakage current. Two breaches of insulation at different locations would potentially expose the user to a leakage current and potential harm. The voltage stressing the insulation would have to be considered in selecting a design to achieve the necessary protection.

While there are many publications that have emerged recently describing various architectures for integrating wiring within garments, WO 2016/131936 A2 (Schwarz), US 215/0359485 A1 (Berg), US 2014/0318699 A1 (Longinotti), WO2017/199026 A1 (Kai), GB 2555592 (Bungay), no attention has been paid to the challenge of insulation. It is notable that a leading supplier of stretchable insulating ink (Dupont™ PE773) that is marketed for wearable applications does not even quote an insulation performance.

The problem therefore is to determine how much insulation is necessary to achieve the desired degree of safety and functional performance and to provide that level of insulation while minimising overall stiffness, weight and thickness of the garment.

In view of the above, it is an object of the present invention to alleviate and mitigate the above disadvantages.

SUMMARY OF THE INVENTION

According to a first aspect, the present invention provides an electrical system comprising conductive and insulating layers for application to a surface of a garment, the electrical system comprising:
  a first insulating layer for attaching to a garment;
  a second insulating layer; and
  an electrically conductive layer encapsulated between the first insulating layer and the second insulating layer.

Preferably, the electrically conductive layer is attached to both the first insulating layer and the second insulating layer. Preferably, the electrically conductive layer is continuously attached to both the first insulating layer and the second insulating layer.

Preferably, the first insulating layer has a voltage withstand of at least 200 VAC or greater and the second insulating layer has a voltage withstand of at least 100 VAC or greater.

Preferably, the first insulating layer has a resistance of at least 200 kΩ when measured with a conductive surface extending over surface of the second insulating layer. Further preferably, the first insulating layer has a resistance of at least 200 kΩ when measured with a conductive surface of greater than 8000 cm$^2$. Further preferably, the first insulating layer has a resistance of at least 200 kΩ when measured with a probe of 8000 mm$^2$.

Preferably, the second insulating layer has a resistance of at least 200 kΩ when measured with a conductive surface extending over surface of the second insulating layer. Further preferably, the second insulating layer has a resistance of at least 200 kΩ when measured with a conductive surface of greater than 8000 cm$^2$. Further preferably, the second insulating layer has a resistance of at least 200 kΩ when measured with a probe of 8000 mm$^2$.

Preferably, the first insulating layer has a thickness of 30 µm or less and a voltage withstand of at least 200 VAC or greater.

Preferably, the first insulating layer has a thickness of 50 µm or less and a voltage withstand of at least 600 VAC or greater.

Preferably, the first insulating layer has a thickness of 100 µm or less and a voltage withstand of at least 1500 VAC or greater.

The second insulating layer may have a thickness of 30 µm or less and a voltage withstand of at least 100 VAC or greater.

The second insulating layer may have a thickness of 50 µm or less and a voltage withstand of at least 600 VAC or greater.

The second insulating layer may have a thickness of 100 µm or less and a voltage withstand of at least 1500 VAC or greater.

Preferably, the first insulating layer has a voltage withstand of at least 1500 VAC or greater and the second insulating layer has a voltage withstand of at least 100 VAC or greater.

Preferably, the first and/or second insulating layer is formed from at least two separately applied and bonded layers of insulating material wherein the number of layers is selected so as to provide a cumulative thickness that gives the insulating layer the required insulation performance.

Preferably, each said separately applied and bonded layer has a dielectric strength of 15 to 20 kV/mm.

Preferably, the thickness of each said separately applied and bonded layer is 8 to 10 µm providing a nominal voltage withstand per layer of 120-200V.

Preferably, each said separately applied and bonded layer is a layer of dielectric ink.

Preferably, said at least two separately applied and bonded layers are formed from at least two separately applied coatings of insulating material wherein a prior coating is allowed to cure before the subsequent coating is applied and wherein the number of coatings is selected so as to provide a cumulative thickness that gives the insulating layer the required insulation performance.

Preferably, the coating is a coating of dielectric ink.

Preferably, an attachment arrangement is provided for attaching the first insulating layer to the garment. The attachment arrangement may comprise an adhesive. Other arrangements for attaching the first insulating layer to the garment are apparent to a person skilled in the art.

According to a second aspect, the invention provides a method of testing an electrical system comprising conductive and insulating layers for application to a surface of a garment, the electrical system comprising
  a first insulating layer for attaching to a garment;
  a second insulating layer; and
  an electrically conductive layer encapsulated between the first insulating layer and the second insulating layer;
  wherein the insulation performance of the first and/or second insulating layer is tested by application of a test voltage between a probe that is connected to the electrically conductive layer and a conductive plate having a defined area that is placed on the relevant insulating layer and measuring the resistance or breakdown voltage therebetween.

Preferably, the conductive plate has a defined area of at least 1000 mm$^2$ or greater. The conductive plate may have a defined area of at least 8000 mm$^2$ Preferably, the conductive plate is shaped to substantially coincide with the shape of the relevant insulating layer.

Preferably, the conductive plate is longer and wider than the insulating layer being tested.

Preferably, the conductive plate is provided as a 3D body form with a conductive surface onto which the insulating layer being tested is applied. Preferably, prior to testing, the relevant insulating layer is attached to a garment and the garment is fitted on the body form with the insulating layer being tested facing the body form.

Features of the first aspect of the invention can be incorporated into the second aspect of the invention as appropriate and vice versa.

DETAILED DESCRIPTION OF THE INVENTION

The invention will now be described with reference to the accompanying drawings, which show, by way of example only, an embodiment of the invention. In the drawings.

Figure 1:
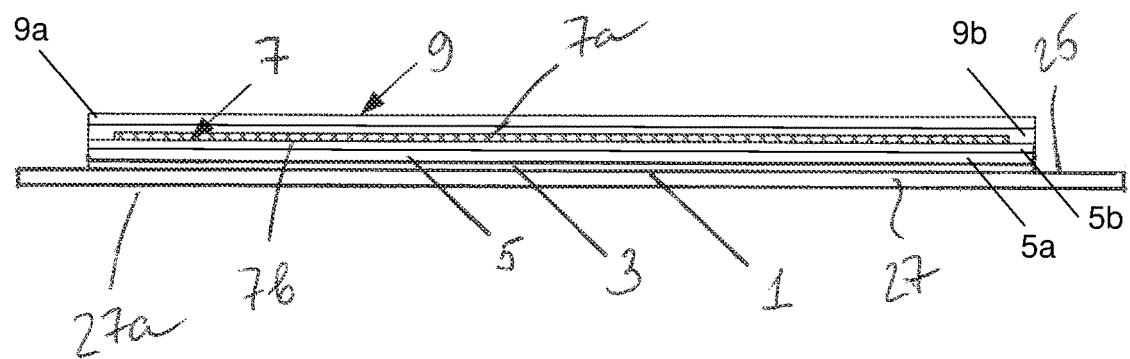
FIG. 1 shows an electrical system attached to a textile substrate.
Figure 2:
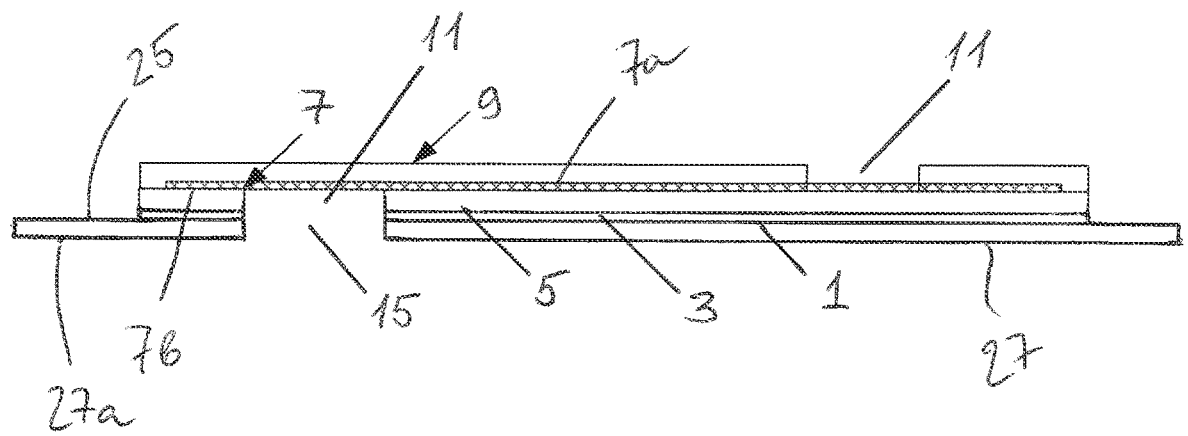
FIG. 2 shows apertures in the insulating layers of the system of FIG. 1 to expose the conductive layer.
Figure 3:
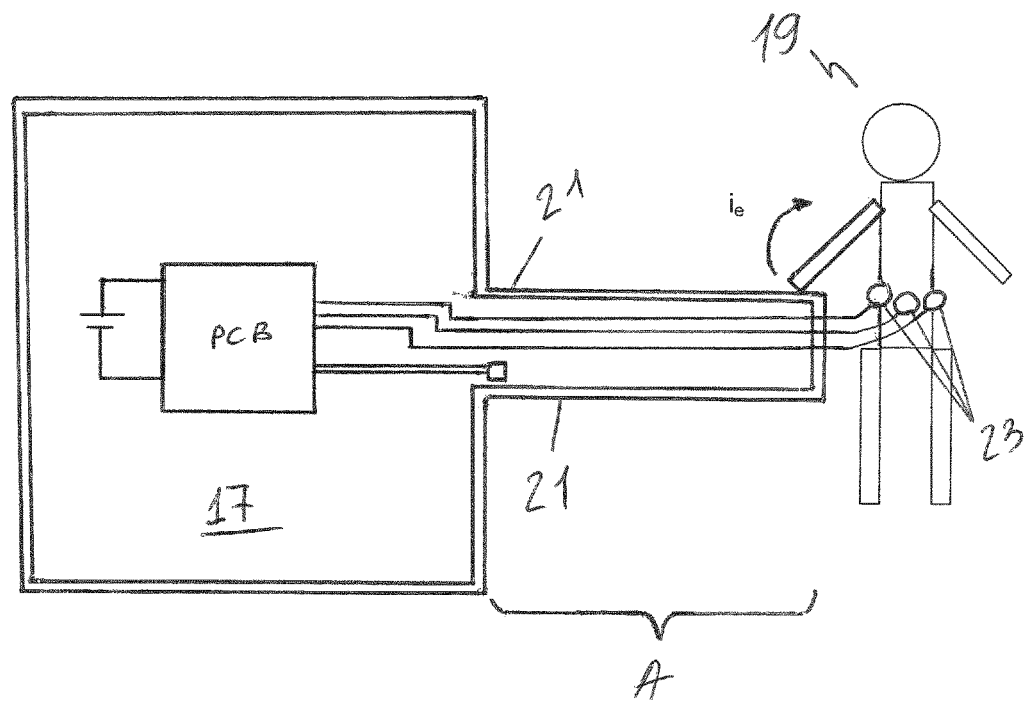
FIG. 3 is an insulation diagram depicting insulation on conductive tracks within a garment that are connected to skin electrodes and potential error current $i_e$ which could flow in the arm if the wearer touched insulation that had failed.

To describe the invention more fully it is useful to consider a specific example namely, transcutaneous electrical stimulation. It will, however, be appreciated that the invention is not limited to such use only. Various other applications will be apparent to the person skilled in the art. The invention will be described with reference to FIGS. 1 to 5. Transcutaneous electrical stimulation is a widely used therapy in which electrical pulses are created within an electronic controller module 17 (see FIG. 3) and delivered to the subject 19 by at least two leadwires 21 of the applied part A in FIG. 3 and corresponding skin attached electrodes 23. The leadwires 21 include embedded wiring or conductive tracks (see conductive layer 7 in FIGS. 1 and 2) which run from the controller module 17 to the electrodes 23 and are insulated to prevent current leakage en-route to the skin electrode 23. These conductive layers can typically be laminated onto a skin-facing side 25 of the garment 27. The insulating layer 9 on the skin facing side 7a of the conductive layer ensures that the current does not leak to the underlying skin when worn, thus causing stimulation at the wrong skin location. Failure of this insulation could cause some discomfort, skin irritation or burning. The insulating layer 5 on the garment facing side 7b of the conductive layer 7 and electrodes prevents current leakage into the garment 27. The first insulating layer 5 and/or the insulating layer 9 may be formed from at least two separately applied and bonded layers 5a, 5b and 9a, 9b, respectively, of insulating material wherein the number of layers is selected so as to provide a cumulative thickness that gives the insulating layer 5 and or the insulating layer 9 the required insulation performance. The garment 27 is typically made of a woven or knitted textile made of an insulating yarn but when wet it could provide a conductive path to the outer surface 27a of the garment 27. If the user makes hand contact with that part of a wetted garment 27 during stimulation, and the insulating layer 5 has failed, then a current ie could flow in the hand, arm and torso area (see FIG. 3). The magnitude of the current flowing in this case would depend on the relative impedance of the hand contact with the electrode contact since they are electrically in parallel. The effect of currents on the human body are set out in IEC 60479 so it is necessary to ensure that any current arising due to failure of insulation is well below limits that cause significant harm.

Figure 4:
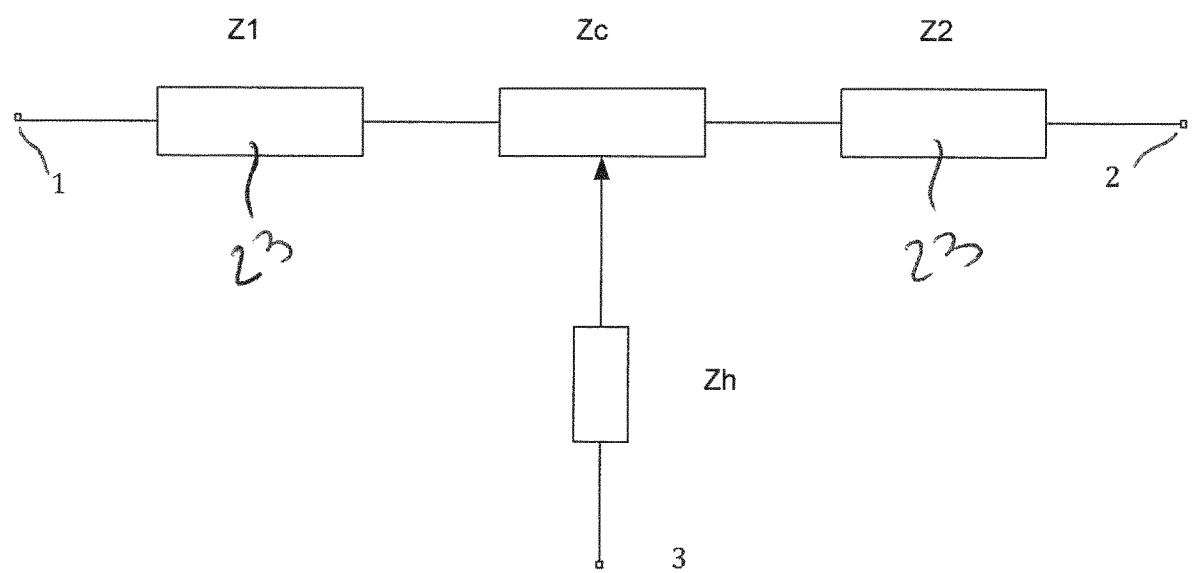
FIG. 4 shows the equivalent circuit of two skin contact electrodes having contact impedance of Z1 and Z2 respectively.
Figure 5:
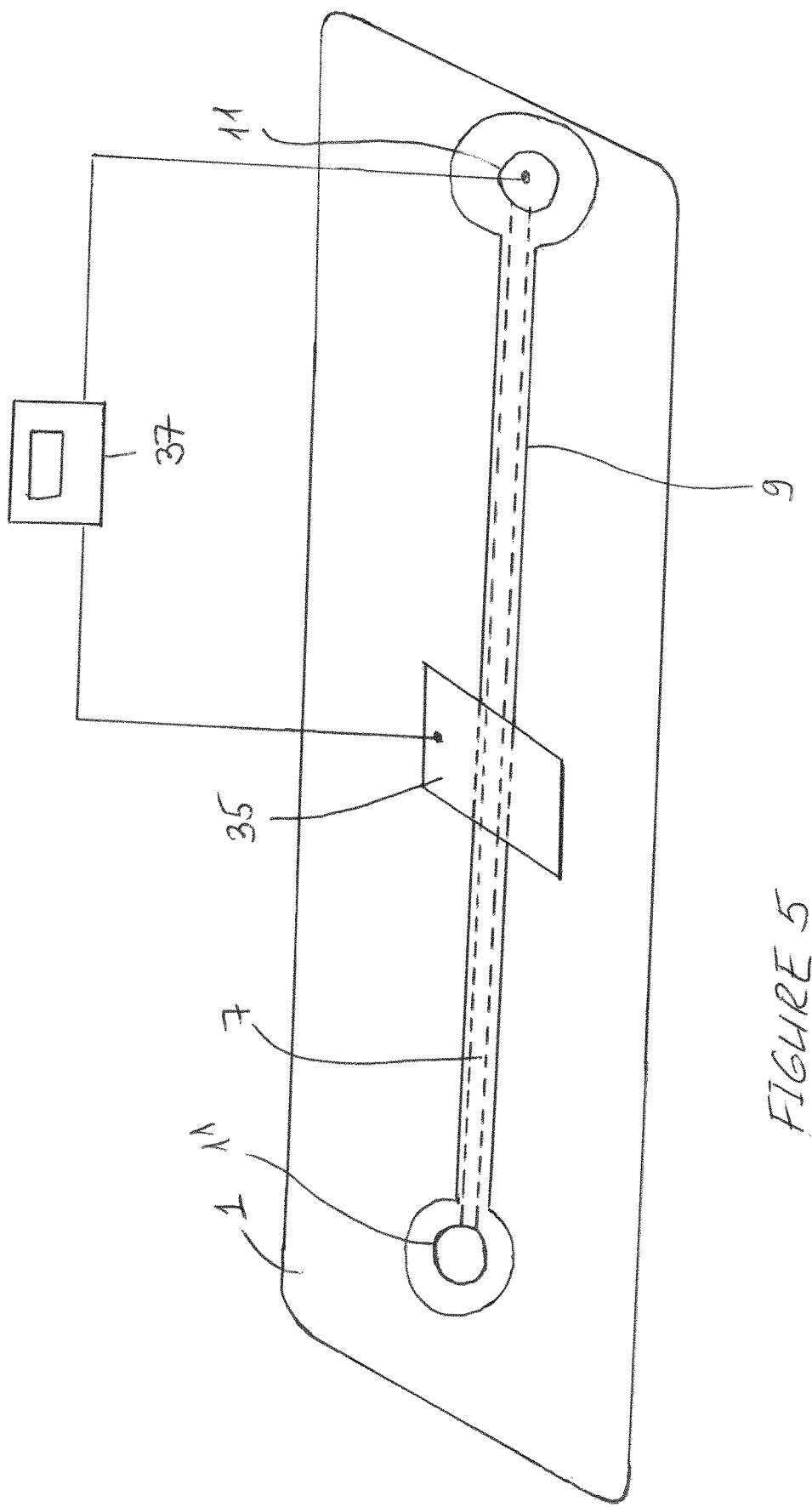
FIG. 5 illustrates testing equipment for testing insulation of the insulating layers of the system.

FIG. 4 shows the equivalent circuit of two skin contact electrodes 23 having contact impedance of Z1 and Z2 respectively. The electrical stimulation is applied between nodes 1 and 2. Zc represents the impedance of the body core between the two electrodes 23 and is normally much less than the skin contact impedances. Zh represents the impedance of hand contact with one of the conductive layers 7 during a fault condition and would be typically higher than Z1 or Z2. The error current $i_e$ flowing in this branch has to be as low as possible to ensure safety.

The inventors have discovered that the voltage stressing this insulation between the conductive layer 7 and the hand is approximately half the voltage across two electrodes 23 in series, because the potential at the hand is effectively the same as the body core as depicted, see equivalent circuit of FIG. 4 representing the electrical impedance of two transcutaneous electrodes 23 in series with the core resistance of the body. It is known that the overall circuit impedance is dominated by the skin contact impedances. For a typical electrical stimulation device that outputs a maximum of 20 Vrms the stress on the insulation is 10 Vrms, even though peak voltages could be up to 50V (electrical stimulation waveforms are usually in the form of low duty cycle pulse trains and the peak pulse amplitude is often a multiple of the root mean square value of the pulse train).

Selecting a safety factor to apply in the design of insulation depends on the risk associated with failure. For low risk applications a factor of 2× could be adequate, leading to a voltage withstand of 20 VAC or a peak voltage withstand of 100V. More preferably, a higher safety factor of 5× is to be used, even for low risk applications. The insulation resistance can be selected to limit the current flow to an upper limit in the absence of breakdown to 100 µA rms at normal operation, therefore 50V/100 µA=500 kΩ.

For higher risk situations the safety factor for voltage breakdown can be increased to 5×, 10×, 20× as appropriate. For currents that can flow across the chest with a risk of fibrillation the voltage withstand may be set as high as 500 VAC, or even 1000 VAC, depending on the estimation of the risk.

Since the risks associated with insulation failure are different between the skin side and the garment side, it may be appropriate to have different insulation performance for each side. Since failure of skin facing insulation only results in skin discomfort, a voltage withstand of 200 VAC may be specified which is more than 20 times the working voltage. For the garment side, the potential for harm is higher so a withstand voltage of 500 VAC is appropriate. The safety standard IEC 60601 ($3^{rd}$ edition) sets out voltage withstand levels for insulation at different working voltages. To provide two means of patient protection it may be necessary to provide insulation at 1000 VAC breakdown voltage.

It should be noted that voltage withstand testing is mostly done with machines operating at mains frequency where the use of "VAC" is appropriate and sufficient. In NMES (Neuro Muscular Electrical Stimulation) the current is pulsed so the use of "Vrms" is more correct.

A typical dielectric ink such as, for example, SE3102 provided by ACI Materials Inc., has a dielectric strength in the range 15 to 20 kV/mm. Special inks with higher dielectric strength are available but flexibility and stretch properties may not be adequate. For a material having 20 kV/mm strength the thickness of one screen print pass is typically 10 µm giving a nominal strength of 200V per layer, so at least three passes are required to build a 500V withstand performance. Flexible inks may be available which can be printed at greater thickness per layer by using different print screen mesh and squeegee parameters.

Screen printing has inherent variability due to mesh marking, mesh stretching, variations in squeegee pressure, angle, speed and ink viscosity. There can also be bubbles which impair insulation performance. Therefore, multiple layers which cumulatively give the required insulation performance are required. Multiple layers typically require a cure time between layers which slows the manufacturing process and so it is desirable to have as few layers as possible.

In addition to being able to withstand a given voltage, it is necessary that the insulation layer provides adequate isolation resistance below the breakdown voltage. The standard IEC 60601 requires that an auxiliary current in normal use be less than 100 μA. Therefore, at a typical working voltage of 20 Vrms, the insulation should be greater than 200 kΩ. The resistance to contact with the hand or finger will depend on the area of contact. The standard IEC 60479 has considered the effect of current on the human and animal body and has defined test contact areas that emulate finger and hand contact. Fingertip contact can be simulated with an area of 250 mm$^2$, while hand contact corresponds to 8000 mm$^2$. A contact area of 1000 mm$^2$ can also be used to simulate finger contact. A suitable insulation test of a garment insulation for finger contact is therefore to measure the resistance (e.g. using an insulation tester 37) at the maximum working voltage between a conductive layer 7 and a surface probe 35 having an area of 1000 mm$^2$ placed on the insulation 5, 9 (see FIG. 5). A similar test, but using a surface probe having an area of 8000 mm$^2$ can be done to test garment insulation for hand contact.

It is necessary to test a structure for voltage breakdown after manufacture to ensure that the insulation layer 5, 9 meets the voltage withstand requirement. The entire surface of the insulation layer 5, 9 needs to be tested and so it is necessary to use a probe which can make contact with every point on the insulation layer 5, 9. A probe or plate can be shaped to coincide with the shape of the insulation layer 5, 9 so that the insulation layer 5, 9 can be tested in one go rather than having to repeat the test multiple times while repositioning a smaller probe. Alternatively, a convenient and rapid means of testing a garment is to fit it onto a conductive body form or mannequin and test the resistance between each terminal of the conductive layer 7 on the garment and the conductive body form. Such a body form could be made of wood, plastic or foam with a conductive coating such as metal foil, conductive textile, conductive paint or ink. It is faster still to connect all terminals of the conductive layer 7 together to form a single electrical node and test the resistance and breakdown voltage between that node and the conductive body form. The garment can be turned inside out to test the performance of the insulation layer 5 on the outwardly facing face of the laminated circuit. Several body forms can be provided to test garments of different size, or the body form could be adjustable.

In garments made of stretch fabrics the electrical system preferably can stretch and relax so that performance of the garment is not impaired. Stretching of the electrical system inevitably reduces cross sectional dimensions in directions normal to the direction of stretch, possibly reducing the insulation withstand voltage. It may therefore be necessary to stretch the test sample on the body form during testing. The size of the body form for the test needs to be selected to match the size of the garment so that the expected stretch is achieved.

Garments can become wet in use and during washing. The insulation layers 5, 9 need to withstand moisture and to prevent ingress of water within the layered structure. It may therefore be necessary to test a wetted garment to ensure safety that voltage withstand and insulation resistance are maintained.

The insulating layers 5, 9 may have apertures 11 to intentionally expose part of the conductive layer 7. The apertures 11 could be formed to allow a connection to be made to the skin, or to a connector or another conductor. In a manner similar to multi-layered printed circuit boards it may be useful to have multiple conductive layers 7 separated by insulating layers 5, 9 but with selective openings 11 to allow the conductive layers 7 make contact at specific points. Apertures 11 in the insulation layers 5, 9 may also be made to allow a connector (not shown) to be attached to the conductive layer 7. Such means of connection could be, for example, a stud compression fastener, a crimp, adhesive, welding, soldering, a simple screwed fastener or another suitable connector. Having made such a connection, it is then necessary to insulate it. An extra layer could be laminated over the joint, such layer having the same insulation properties as the insulation layer to which it is attached. Other means could include overmoulding or resin that is injected or sprayed onto the joint.

There are several methods available for creating the insulating and conductive layers on a garment. WO 2017/199026 A1 (Kai et al) describes a process of screen printing successive layers on a textile. GB2555592 (Bungay et al) describes an alternative method whereby multiple layers are laid down on a transfer print substrate and then applied to the garment using heat or pressure. Equally, layers can be formed by placing and adhesively bonding or welding shaped layers of insulating and conducting materials on top of each other. For example, a first insulating layer, for example insulating layer 5, could be an insulating TPU having a thickness in the order of 100 to 200 μm. The conducting layer 7 could be a conductive thread, a conductive textile, a metal foil or could be a conductive ink pattern printed onto the first insulating layer 5. The second insulating layer, for example insulating layer 9, could be another shaped layer of insulating TPU or other polymer or printed dielectric ink having a thickness less than 100 μm. The whole assembly can be adhesively bonded to the fabric via the adhesive layer 3.

While much of the forgoing describes a layered structure of insulating layers 5, 9 and conducting layers 7 that are applied to the skin facing side 25 of the garment, it is also possible to apply the structure to the outside surface 27a of the garment, or even in a layer between two textile layers 27. The insulation co-ordination would have to take account of the risk profile of the particular application.

It will be appreciated by those skilled in the art that variations and modifications can be made without departing from the scope of the invention as defined in the appended claims.

The invention claimed is:

1. An electrical system comprising conductive and insulating layers for application to a surface of a garment, the electrical system comprising:
   a first insulating layer for attaching to a garment;
   a second insulating layer; and
   an electrically conductive layer encapsulated between the first insulating layer and the second insulating layer, wherein the first insulating layer has a voltage withstand of at least 200 VAC or greater and the second insulating layer has a voltage withstand of at least 100 VAC or greater.

2. An electrical system of claim 1, wherein the first insulating layer has a resistance of at least 200 kΩ when measured with a surface probe having an area of greater than 8000 cm$^2$.

3. An electrical system of claim 1, wherein the second insulating layer has a resistance of at least 200 kΩ when measured with a surface probe extending over surface of the second insulating layer.

4. An system of claim 1, wherein the first insulating layer has a thickness of 30 μm or less and a voltage withstand of at least 200 VAC or greater.

5. An electrical system of claim 1, wherein the first insulating layer has a thickness of 50 μm or less and a voltage withstand of at least 600 VAC or greater.

6. An electrical system of claim 1, wherein the first insulating layer has a thickness of 100 μm or less and a voltage withstand of at least 1500 VAC or greater.

7. An electrical system of claim 1, wherein the second insulating layer has a thickness of 30 μm or less and a voltage withstand of at least 100 VAC or greater.

8. An electrical system of claim 1, wherein the second insulating layer has a thickness of 50 μm or less and a voltage withstand of at least 600 VAC or greater.

9. An electrical system of claim 1, wherein the second insulating layer has a thickness of 100 μm or less and a voltage withstand of at least 1500 VAC or greater.

10. An electrical system of claim 1, wherein the first insulating layer has a voltage withstand of at least 1500 VAC or greater and the second insulating layer has a voltage withstand of at least 100 VAC or greater.

11. An electrical system of claim 1, wherein one or each of the first and second insulating layers is formed from at least two separately applied and bonded layers of insulating material wherein the number of layers is selected so as to provide a cumulative thickness that gives the insulating layer the required insulation performance.

12. An electrical system of claim 11, wherein each said separately applied and bonded layer has a dielectric strength of 15 to 20 kV/mm.

13. An electrical system of claim 12, wherein the thickness of each said separately applied and bonded layer is 8 to 10 μm providing a nominal voltage withstand per layer of 120-200V.

14. An electrical system of claim 11, wherein each said separately applied and bonded layer is a layer of dielectric ink.

15. An electrical system of claim 1, wherein the electrically conductive layer is attached to both the first insulating layer and the second insulating layer.

16. An electrical system of claim 15, wherein the electrically conductive layer is continuously attached to both the first insulating layer and the second insulating layer.

17. An electrical system of claim 1, wherein an attachment arrangement is provided for attaching the first insulating layer to the garment.

18. An electrical system of claim 17, wherein the attachment arrangement comprises an adhesive.

19. A method of testing an electrical system comprising conductive and insulating layers for application to a surface of a garment, the electrical system comprising
a first insulating layer for attaching to a garment;
a second insulating layer;
an electrically conductive layer encapsulated between the first insulating layer and the second insulating layer; and
wherein the insulation performance of one or each of the first and second insulating layer is tested by application of a test voltage between the electrically conductive layer and a surface probe having a defined area that is placed on the first insulating layer or second insulating layer and measuring the resistance or breakdown voltage therebetween.

20. A method of claim 19, wherein the surface probe has a defined area of at least 1000 mm$^2$ or greater.

21. A method of claim 20, wherein the surface probe is shaped to substantially coincide with the shape of the relevant insulating layer.

22. A method of claim 21, wherein the surface probe is longer and wider than the insulating layer being tested.

23. A method of claim 19, wherein the surface probe is provided as a 3D body form onto which the insulating layer being tested is applied.

24. A method of claim 23, wherein, prior to testing, the relevant insulating layer is attached to a garment and the garment is fitted on the body form with the insulating layer being tested facing the body form.

* * * * *